US00RE37999E

(19) United States

(12) Reissued Patent

Tipton et al.

(10) Patent Number: US RE37,999 E

(45) **Date of Reissued Patent: *Feb. 18, 2003**

(54) 20-(B)-20,25-DIHYDROPEROXY-3β-HYDROXYCHOLEST-5-ENE AND 20-(S)-20, 25-DIHYDROPEROXY-3β-HYDROXYCHOLEST-5-ENE

(75) Inventors: Carl L. Tipton, Ames, IA (US); Meiling Shih, Port Jefferson, NY (US)

(73) Assignee: Iowa State University Research Foundation, Inc., Ames, IA (US)

( * ) Notice: This patent is subject to a terminal disclaimer.

(21) Appl. No.: 07/829,945

(22) Filed: Feb. 3, 1992

Related U.S. Patent Documents

Reissue of:

(64) Patent No.: 4,900,726
Issued: Feb. 13, 1990
Appl. No.: 07/262,613
Filed: Oct. 26, 1988

(51) Int. Cl.[7] ..... A61K 31/56; C07J 9/00

(52) U.S. Cl. ..... 514/182; 514/824; 552/546

(58) Field of Search ..... 514/182, 824; 552/546

(56) References Cited

U.S. PATENT DOCUMENTS 4,789,670 A 12/1988 Tipton et al. ..... 514/182

OTHER PUBLICATIONS

Bader et al., "Intracellular Calcium Regulation," Manchester Univ. Press, 406–423 (1986).

Highley et al. I, "Comparative Atherogenic Effects of Cholesterol and Cholesterol Oxides," Elsevier Sci. Pub. Ireland, Ltd. 91–104 (1986).

Highley et al. II, "Comparative Aterogenic Effects of Cholesterol and Cholesterol Oxides," Chemical Abstract, vol. 106:31761k (1986).

Honda et al., "Structures of Thronasterols A and B (Biologically active Glycosides from Asteroidia, XI)," Tetrahedron Letters, vol. 27, No. 29:3369–3372 (1986).

Leung et al., "Ophiobolin A, A Natural Product Inhibitor of Calmodulin" J. Bio. Chem. vol. 259, Mar. 10, 2742–2747 (1984).

Nes et al., "Conformational Analysis of the 17(20) Bond of 20–Keto Steroids," J. Org. Chem. vol. 41, No. 9, 1652, 1652 (1976).

The Merck Index, "An Encyclopedia of Chemicals and Drugs," 9th ed., 2171 (1976).

Mathur et al., "A Defect in Mobilization of Cholesteryl Esters in Rabbit Macrophages," Biochimica et Biophysica Acta, 834:48–58 (1985).

Mijares et al., "Studies on the C–20 Epimers of 20–Hydroxycholesterol,"J. Org. Chem. vol. 32:810–812 (Mar. 1967).

Perkins et al., "Dietary Fats and Health," American Oil Chemist's Society, 919–933 (1983).

Smith et al, "Cholesterol Autoxidaton," Plenum Press, NY, 238, 239 (1981).

Suckling et al., "Role of acyl–CoA:cholesterol acyltransferase in Cellular Cholesterol Metabolism," J. Lipid Research, 26:647–671 (1985).

Teng et al., Sterol Metabolism. XX. Cholesterol 7β–Hydroperoxide, J. Org. Chem. vol. 38, No. 1, 119–123 (1973).

Tipton et al. I, "Federation Proceedings," 71st Annual Meeting, Washington, D.C., vol. 46, No. 3, 416 (Mar. 1987).

Tipton et al. II, "Cholesterol Hydriperoxide Inhibit Calmodulin and Suppress Atherogenesis in Rabbits," Biochem. Biophy, Research Comm., vol. 146, No. 3, 1166–1172 (Aug. 1987).

Tipton et al. III, "Cholesterol Hydroperoxides Inhibit Calmodulin and Suppress Atherogenesis in Rabbits," Chemical Abstract vol. 107:36 (1987).

Van Lier et al. I, J. Mechanism of Cholesterol Side–Chain Cleavage: Enzymic Rearrangement of 20β Hydroperoxy–20–Isocholesterol to 20 β–21–Dihydroxy–20–Isocholesterol Org. Chem. vol. 35, No. 8 p. 2627–2632 Van Lier et al.

Van Lier et al. II, Febslett. 70:23–27 (1979).

*Primary Examiner*—Kimberly Jordan

(74) *Attorney, Agent, or Firm*—Tilton, Fallon, Lungmus & Chestnut

(57) ABSTRACT

A method is provided for suppressing atherogenesis in which [a cholesterol 20-hydroperoxide is administered, which is preferably one or both of the novel compounds: 20(R)-hydroperoxy-25-hydrocholesterol and 29(S)-hydroperoxy-25-hydrocholesterol] *20(R)-hydroperoxy-25 hydrocholesterol and 20(S)-hydroperoxy-25-hydrocholesterol are administered. The compositions 20(R)-hydroperoxy-25-hydrocholesterol and 20(S)-hydroperoxy-25-hydrocholesterol are also provided.*

8 Claims, No Drawings

20-(B)-20,25-DIHYDROPEROXY-3β-HYDROXYCHOLEST-5-ENE AND 20-(S)-20,25-DIHYDROPEROXY-3β-HYDROXYCHOLEST-5-ENE

Matter enclosed in heavy brackets [ ] appears in the original patent but forms no part of this reissue specification; matter printed in italics indicates the additions made by reissue.

FIELD OF INVENTION

The field of the invention is medicine agents and methods for combatting atherogenesis.

BACKGROUND OF INVENTION

The role of cholesterol oxidation products in atherogenesis has long been a controversial topic. Peng and Taylor (1983), for example, hypothesized that cholesterol oxidation products may be responsible for an initial arterial cell injury that eventually results in atherosclerosis. On the other hand, Higley et al. (1986) disputed that hypothesis, claiming instead that oxidized cholesterol is substantially less atherogenic than purified cholesterol. The analysis of the oxidized cholesterol shown in Table 1 of Higley et al. indicated the presence of diols and epoxides (78%) as the major oxidized compounds with a minor amount of hydroperoxide (18%) identified as 7α-hydroperoxide.

Hypercholesteroloemia is widely considered to be a major risk factor for the development of atherosclerosis. The lowering of blood cholesterol levels has therefore been an important goal in the search for ways to prevent or treat atherosclerosis. Medicinal agents reported as reducing development of athersclerotic lesions typically result in the lowering of blood cholesterol levels. Beneficial agents which do not affect blood cholesterol are rare. But Bell and Schaub (1986) have reported that chlorpromazine reduced the development of such lesions in rabbits fed an atherogenic diet without lowering of blood cholesterol. Chlorpromazine may function as an inhibitor of calmodulin (Gietzen, 1986) but it is classified pharmacologically as a tranquilizer and sedative (Merck Index, 1976), and therefore is not likely to be useful as a treatment for atherosclerosis.

Tipton, et al. (1987), have reported that a mixture of cholesterol auto-oxidation products prepared from an aged sample of cholesterol inhibits calmodulin irreversibly in a $Ca^2$+-dependent reaction. The reactive material was destroyed by chemical reduction. It was concluded that the calmodulin inhibition was due to one or more cholesterol hydroperoxides. The mixture of cholesterol hydroperoxides was further purified by chromatography and used in feeding experiments with rabbits. Three diets were compared, one with added cholesterol, one with added cholesterol hydroperoxides, and the third with both the cholesterol and cholesterol hydroperoxides. The diet containing cholesterol alone was found to have caused extensive atheroma formation, while the addition of the cholesterol hydroperoxides to the cholesterol diet markedly reduced atheroma formation. The cholesterol hydroperoxides were not found to lower cholesterol concentration in blood plasma, liver or heart. In a related experiment, it was found that the chemically reduced hydroperoxides were not effective in reducing atheroma formation.

Cholesterol oxidizes readily in contact with air, and the oxidation proceeds at ambient room temperature. The oxidation products as initially formed are largely cholesterol hydroperoxides. See Smith, "Cholesterol Autooxidation" (1981, Plenum Press, New York). This reference lists the initial auto-oxidation products in Table 11, pages 238 to 239. These included 3β-hydroxycholest-5-ene-7α-hydroperoxide; 3β-hydroxycholest-5-ene-7β-hydroperoxide; and 3β-hydroxycholest-5-ene-25-hydroperoxide, which is presently preferred for use in this invention. Other hydroperoxides included 3β-hydroxycholest-5-ene-17-hydroperoxides; 3β-hydroxycholest-5-ene-20-hydroperoxides; 3β-hydroxycholest-5-ene-22-hydroperoxides; and 3β-hydroxycholest-5-ene-24-hydroperoxides.

When it is desired to accelerate the oxidation of cholesterol to hydroperoxides, a photochemical oxidation procedure can be employed as described by Schenk et al. (1958). This reference describes the preparation and isolation of 3β-hydroxycholest-5-ene-7α-hydroperoxide. The 7-β isomer of this compound can be synthesized and isolated as described by Teng et al. (1973). Other cholesterol hydroperoxides can be prepared as an oxidized mixture, and separated by fractionation. See van Lier et al. (1970).

SUMMARY OF INVENTION

This invention is based in part on the discovery of a novel class of cholesterol hydroperoxide compounds in which the hydroperoxide group is in the 20-position and the compounds also contain other added oxygenation. As far as is known, no oxidized derivatives of cholesterol have heretofore been reported containing [a 20-hydroperoxy group together with a 25-hydroxyl group. An example of such novel compounds is 20-hydroperoxy-25-hydroxycholesterol which has two isomeric forms (R and S). Specific compounds are 20(R)-hydroperoxy-25-hydroxycholesterol and 20(S)-hydroperoxy-25-hydrocholesterol. These compounds can also be named as: 20-(R)-hydroperoxy-cholest-5-ene-3β,25-diol, and 20(S)-hydroperoxy-cholest-5-ene-3β,25-diol.] *hydroperoxy groups at two positions. An example of such novel compounds is 20,25-dihydroperoxy cholesterol which has two isomeric forms (20 R and 20 S). Specific compounds are 20-(R)-20,25-dihydroperoxycholesterol and 20-(S)-20,25-dihydroperoxycholesterol. These compounds can also be named as: 20-(R)-20,25-dihydroperoxy-3β-hydrocholest-5-ene and 20(S)-20,25-dihyroperoxy-3β-hydroxycholest-5-ene.*

The 20-hydroperoxy cholesterol compounds of this invention are highly active as calmodulin inhibitors, and also display a high level of activity as inhibitors of acyl-CoA:cholesterol acyl transferase (ACAT). ACAT is an index for anticholesterol therapeutic agents (Suckling et al., 1985). The novel compounds of this invention are therefore believed to be useful as therapeutic agents for suppressing atherogenesis in human patients.

EXPERIMENTAL BASIS OF INVENTION

Isolation

The starting material is cholesterol that has been "aged" in air at room temperature for a long time (in this case 20 years) or cholesterol that has been heated at 55–60 C. in the dark in a thin layer for 14 days.

The starting material is dissolved in boiling methanol, 30 ml per gram of starting material; the solution is cooled slowly to 4 C. to allow crystallization of unchanged cholesterol. The cholesterol is removed by vacuum filtration and the filtrate is reduced to one eighth the original volume by distillation on a rotary evaporator under reduced pressure. After cooling the concentrated filtrate to 4 C., a second crop of cholesterol is removed by vacuum filtration. The filtrate from this step is extracted three times with hexane and the methanol-rich (lower) layer is evaporated to dryness under vacuum with a rotary evaporator to yield 2.5 g of residue from 50 g of starting material.

This mixture is fractionated by flash chromatography on silicic acid (60–230 mesh, 200 g) eluted with hexane, 2-propanol mixtures according to the following protocol:

| hexane-2-propanol ratio, v/v | volume, ml. |
|---|---|
| 12:1 | 260 |
| 11:1 | 240 |
| 10:1 | 440 |
| 9:1 | 500 |
| 6:1 | 280 |

Elution was at the rate of 50 mL/min and 50 mL fractions were collected. The desired product elutes in fractions 16–21, with hexane:2-propanol 10:1 v/v. The combined fractions 16–21 are evaporated to dryness to yield about 0.3 g of material which is then rechromatographed on silicic acid (200–400 mesh, 75 g) with hexane and 2-propanol mixtures according to the following protocol:

| hexane-2-propanol ratio, v/v | volume, ml. |
|---|---|
| 10:1 | 440 |
| 9:1 | 250 |
| 8:1 | 270 |
| 7:1 | 240 |
| 5:1 | 240 |

The flow rate is 20–25 mL/min. After the first 100 mL of solvent, one-minute fractions are collected. Elution of the hydroperoxides is monitored by thin-layer chromatography on silica gel, with benzene and ethyl acetate 3:2 (v.v) as the developing solvent. Hydroperoxides are detected by spraying the plates with 1% N,N-dimethyl-p-phenylenediamine in methanol and water 1:1 (v/v) containing 1% acetic acid. The desired product elutes in fractions 25–31, with hexane:2-propanol 8:1 v/v and the yield is 40 mg.

This mixture is then fractionated by reverse-phase high-performance liquid chromatography on an Ultrasphere (Beckman Instrument Co.) octadecylsilane-treated silica column, 4.6 mm×25 cm. Elution is with acetonitrile:water 6:4 v/v and the elution is monitored by measuring absorbance at 210 nm. Major peaks eluting at about 12.6 and 15.8 min are collected and designated compounds A and B, respectively. The yields from 50 g "aged" cholesterol are 8.9 mg A and 11.9 mg B.

The inhibition of calmodulin activity by A and B were measured using the method described by Leung et al. (1984) and the results are shown in Table 1.

TABLE 1

The inhibitory effect of hydroperoxides A and B on calmodulin. The compounds, in the amounts specified, were preincubated with 0.3 units of calmodulin, followed by calmodulin assay at 30 C. for 30 min.

| Treatment | nmole P produced[i] | % inhibition |
|---|---|---|
| Compound A: | | |
| 1 μg | 12.1 | 92 |
| 0.1 μg | 16.1 | 68 |
| 0.01 μg | 22.9 | 28 |
| Compound B | | |
| 1 μg | 13.8 | 81 |
| 0.1 μg | 17.3 | 61 |
| 0.01 μg | 26.9 | 4 |
| Control | 27.5 | 0 |
| Control + EDTA | 10.7 | 100 |

Mass spectra of compounds A and B were obtained by desorption/chemical ionization in isobutane. The fragments used in elucidating the structure are listed in Table 2.

TABLE 2

Mass spectra of Compounds A and B.

| | Relative Intensity | |
|---|---|---|
| m/z | A | B |
| 433 | 3.1 | 0.1 |
| 417 | 3.9 | 0.5 |
| 399 | 9.0 | 9.0 |
| 401 | 1.8 | 1.2 |
| 383 | 8.7 | 7.8 |
| 365 | 8.3 | 9.2 |
| 317 | 66.0 | 42.3 |
| 299 | 73.9 | 52.1 |
| 273 | 73.8 | 74.5 |
| 255 | 100.0 | 100.0 |

The two compounds have very similar fragmentation patterns, suggesting that they are isomers. The fragments listed [suggest that the molecular weight is 434, produced by the addition of three atoms of oxygen to cholesterol. Fragments with m/z 417, 399, 401, 383, and 365 are produced by losses of one or two molecules of water, and/or loss of a molecule of hydrogen peroxide, from the (M+1) ion, m/z 435. The fragment with m/z 317 is produced by O—O cleavage of the —OOH group at C-20 combined with cleavage of the C-20, C-22 bond; m/z 299 is formed by loss of water from this ion. The fragment with m/z 273 is formed by loss of the side-chain (cleavage between C-17 and C-20) and m/z 255 is formed by loss of water from m/z 273. These fragments show that only the side-chain has been modified in formation of these compounds from cholesterol, that three oxygen atoms have been added, in the form of an alcohol and a hydroperoxy group, and that the most likely site of attachment of the hydroperoxy group is at C-20.] *are best interpreted as arising from fragmentation of a molecule of molecular weight 450, produced by the addition of four atoms of oxygen to cholesterol m/z 433* ($M+1—H_2O$); *417* ($M+1—H_2O_2$); *399* ($M+1—H_2O—H_2O_2$); *365* ($M+1—H_2O—2H_2O_2$; *317* ($M+1—OH—C_{22}$ *to* $C_{27}$; *299* ($317—H_2O$); *273* ($M—C_{20}$ *to* $C_{27}$); *255* ($273—H_2O$). *These fragments show that only the side-chain has been modified in formation of these compounds from cholesterol, and that four atoms of oxygen have been added, in the form of two hydroperoxy groups.*

$^1$H-NMR spectra of the compounds and of cholesterol were obtained and are compared with the spectra of two diastereomers of 20-hydroperoxycholesterol, reported by van Lier and Rousseau (19760, in Table 3.

TABLE 3

$^1$H-NMR Spectra of Compounds A and B and reference compounds

| | Chemical Shift, ppm | | | 20-OOH* | |
|---|---|---|---|---|---|
| | Cholesterol | A | B | α | β |
| C-18 | 0.674s | 0.783s | 0.830s | 0.79s | 0.83s |
| C-19 | 1.003s | 1.008s | 1.010s | 1.02s | 1.02s |
| C-21 | 0.810d, J=6.6 | 1.248s | 1.249s | 1.25s | 1.25s |
| C-26, 27 | 0.858d, J=6.9<br>0.862d, J=6.6 | 1.237s | 1.235s | 0.88d | 0.88d |

*20-hydroperoxycholesterol isomers, from van Lier and Rousseau (1976).

The signal for C-21, which is a doublet in the spectrum of cholesterol, is a singlet in the spectra of compounds A and B and the isomers of 20-hydroperoxycholesterol, showing that the proton on C-20 has been replaced. Similarly, the signals for C-26 and C-27, doublets in the spectra of cholesterol and 20-hydroperoxycholesterol, coalesce to a singlet in the spectra of compounds A and B, showing that the proton on C-25 has been replaced.

[The hydroperoxy group is shown to be at C-20, and the hydroxy group at C-25, by the following comparisons (Tables 3 and 4).] *The stereochemistry at C-20 is deduced by the following comparisons (Tables 3 and 4).*

TABLE 4

$^1$H-NMR spectra of the products of reduction of compounds A and B by $NaBH_4$ and of reference compounds.

| | Chemical Shift, ppm | | 20-OH* | |
|---|---|---|---|---|
| | Reduced A | Reduced B | α | β |
| C-18 | 0.87 | 0.87 | 0.87 | 0.87 |
| C-21 | 1.29 | 1.15 | 1.28 | 1.13 |

*20-Hydroxycholesterol isomers, from Honda nd Komori, 1986 and Nes and Varkey, 1976.

The $^1$H-NMR spectra of 20-α- & β-hydroxycholesterols have been compared (Honda and Komori, 1986; Nes and Varkey, 1976). Both epimers show the same chemical shift for protons on C-18, while the protons on C-21 have different chemical shifts in the two epimers. On the other hand, van Lier and Rousseau report that in the two epimers of 20-hydroperoxycholesterol, the chemical shift for the C-21 protons is the same, while the chemical shift for the C-18 protons is affected by the stereochemistry at C-20. Compounds A and B have the same chemical shift at C-21 but differ at C-18 while the products of reduction of the hydroperoxides to alcohols have the same chemical shift at C-18 and differ at C-21. [Therefore the hydroperoxy group is at C-20. The stereochemistry at C-20 of Compound A and B can also be deduced from the data in Tables 3 and 4.] The chemical shift at C-18 of compound A is further upfield than that of compound B and therefore by analogy with the epimers of 20-hydroperoxycholesterol, compound A is the [α isomer (cholest-5-ene-3β,20S-diol)] α *isomer (20-(S)-20, 25-dihdroperoxy-3β-hydroxycholest-5-ene)*, and compound B is the [β isomer (cholest-5-ene-3β,20R-diol)] β *isomer (20-(R)-20,25-dihydroperoxy-3β-hydroxycholest-5-ene)*. Comparison of the spectra of the reduction products to those of the epimers of 20-hydroxycholesterol confirms this assignment of stereochemistry.

COMMERCIAL PRACTICE OF INVENTION

The novel 20-hydroperoxide cholesterol compounds are prepared, purified and isolated as described above for use as therapeutic agents in suppressing atherogenesis in human patients. [The preferred compounds are 20(S)-hydroperoxy-cholest-5-ene-3β,25-diol and 20(R)-hydroperoxy-cholest-5-ene-3β-25 diol.] *The preferred compounds are 20-(S)-20, 25-dihydroperoxy-3β-hydroxycholest-5-ene and 20-(R)-20, 25-dihydroperoxy-3β-hydroxycholest-5-ene.* These compounds may be used separately or in admixture. 20-hydroperoxy cholesterol compounds of this invention are characterized by being potent inhibitors of calmodulin, for example, by the assay described by Leung et al. (1984). They also demonstrate a high level of inhibitory activity in the ACAT assay, as described by Mather, et al. (1985).

The amount of cholesterol 20-hydroperoxide to be administered can be related to the body weight and/or the blood cholesterol level of the patient. A sufficient amount of the cholesterol hydroperoxide should be administered to be effective for reducing aortal deposit of cholesterol. For example, from 0.5 to 25 milligrams (mg) of cholesterol 20-hydroperoxide can be orally administered per kilogram (kg) of body weight per 24 hours. The administration should be on a regular basis for a period of time as required to prevent or treat cholesterol-induced atherogenesis. The cholesterol 20-hydroperoxide may be prepared in the form of tablets or capsules. The 20-hydroperoxide compounds can be combined with tabletting compositions, viz. dextrose or sucrose, and formed into tablets. Conveniently, the tablets may contain an amount of the cholesterol hydroperoxide so that 2 to 4 tablets per 24 hours may be taken. For example, each tablet may contain 12.5 mg for a two tablet dose, or 6.25 mg of cholesterol hydroperoxide for a four tablet dose per 24 hours, or other effective dose amounts.

The cholesterol-20-hydroperoxides may also be prepared in capsule dose form. The capsules can contain only the cholesterol 20-hydroperoxide, or it may be admixed with a pharmaceutical extender or diluent, such as lactose, dextrose, etc.

For oral administration, either in the form of tablets or capsules, the hydroperoxides may be administered in doses of from about 0.5 to 25 mg of cholesterol 20-hydroperoxide per patient per 24 hours. If the cholesterol 20-hydroperoxide composition includes oxidized derivatives of cholesterol other than the 20-hydroperoxides, dosage should be on the basis of the 20-hydroperoxide content only.

The administration of cholesterol 20-hydroperoxide can be monitored if desired. For example, a blood sample can be obtained and the serum separated with the lipoproteins therein. A portion of the serum can then be subjected to a cAMP-phosphodiesterase assay (Sharma & Wang, 1979) to measure calmodulin inhibition.

EXPERIMENTAL EXAMPLES

The effects of cholesterol hydroperoxides on the esterification of cholesterol in mouse peritoneal macrophages was tested as follows:

Monolayers of mouse peritoneal macrophages were pretreated with various concentration of [20-(S)-hydroperoxy-cholest-5-ene-3β,25-diol hydroxycholesterol (A) or 20-(R)-hydroperoxycholest-5-ene-3β,25 diol (B)] *20-(S)-20,25-dihydroperoxy-3β-hydroxycholest-5-ene-(A) or 20-(R)-20, 25-dihydroperoxy-3β-hydroxycholest-5-ene (B)* at 37° C. After 15 min preincubation, medium M199 providing 2.5% fetal calf serum, acetyl-LDL (25 μg protein/ml) and $^3$H-oleate (0.25 μCi/ml) was added to the culture dishes. After 6 hr of incubation with 5% $CO_2$ at 37° C. the cellular lipids were extracted. This layer chromatography was used to separate cholesteryl ester from other lipid classes before the radioactivity was determined. The activities reported have been corrected for losses during chromatography and elution of the thin-layer plates. The results are shown in Table 5.

TABLE 5

| Concentration of hydroperoxide, μM | Compound A | Compound B |
|---|---|---|
| | Counts per min $^3$H incorporated into cholesteryl ester | |
| 0 | 43433 | 48023 |
| 0 | 48393 | 30604 |
| 2.5 | 55816 | 41574 |
| 2.5 | 47673 | 34918 |
| 5 | 59136 | 32751 |
| 10 | 33700 | 25140 |
| 10 | 29618 | 16252 |
| 25 | 14510 | 7752 |
| 25 | 17621 | 6232 |
| 50 | 6059 | 4073 |
| 50 | 6059 | 4073 |
| 75 | 5074 | 3177 |
| 75 | 5047 | 3385 |
| 100 | 2830 | 4427 |
| 100 | 3970 | 2401 |

Data in Tables 5, 6, and 7 can be supplied in concentration units if preferred. It is a simple conversion which only requires the specific activities of $^3$H-oleate and $^{14}$C-oleoyl coenzyme A, which are given.

In a further experiment, the time course of incorporation of $^3$H-oleate into the same cholesterol esters by mouse peritoneal macrophages was studied. Mouse peritoneal macrophages were gorwn in M199 medium containing 2.5% fetal calf serum and acetyl-LDL (25 μg protein/ml) for 18 hr at 37° C. The medium was then replaced by M199 containing 2.5% fetal calf serum; $^3$H-oleate with 50 μM compound A or 25 μM compound B or no hydroperoxide. At the time intervals indicated, the medium was aspirated and the cellular lipid was extracted and analyzed by thin-layer chromatography. The results are shown in Table 6.

TABLE 6

| Time | Counts per minute in cholesterol ester | | |
|---|---|---|---|
| min. | Control | Compound A | Compound B |
| 5 | 3003 | 2627 | 2218 |
| 5 | 3414 | 1994 | 1256 |
| 10 | 4632 | 2462 | 2560 |
| 10 | 4324 | 3092 | 2019 |
| 20 | 8461 | 6049 | 4788 |
| 20 | 15126 | 5223 | 3245 |
| 30 | 8289 | 4007 | 3202 |
| 30 | 10718 | 2937 | 2943 |
| 60 | 40595 | 4088 | 5054 |
| 60 | 16474 | 5295 | 7341 |
| 120 | 38663 | 7269 | 7534 |
| 120 | 40071 | 10036 | 9160 |
| 240 | 57642 | 19627 | 18532 |
| 240 | 66614 | 17564 | 15819 |

These results of Table 6 show that the reaction is linear with time up to at least 4 hours. The inhibition due to the Compounds A and B is apparent at the shortest time samples (5 min.).

In another experiment, the inhibition of [acrylCoenzyme-A:cholesterol] *acyl-Coenzyme-A:cholesterol* acyltransferase (ACAT) by cholesterol hydroperoxides, compounds A and B was used. Mouse liver microsomes (140 μg protein/assay) were treated with various concentrations of compounds A and B for 15 min prior to starting the assay by the addition of $^{14}$C-oleoyl-Coenzyme A (41 μM, 0.068 μCi/assay). The reaction was carried on at 37° C. for exactly 5 min. then terminated by the addition of chloroform and methanol. The cellular lipids were extracted and separated by thin-layer chromatography. The results are shown in Table 7.

TABLE 7

| Concentration, | Counts per minute in cholesterol esters | |
|---|---|---|
| μM | Compound A | Compound B |
| 0 | 5529 | 4928 |
| 0 | 5250 | 5190 |
| 2.5 | 4702 | 4557 |
| 2.5 | 4651 | 3518 |
| 5 | 3420 | 2336 |
| 5 | 4109 | 1786 |
| 10 | 3033 | 2499 |
| 10 | 5422 | 1896 |
| 16.7 | 1643 | 920 |
| 16.7 | 1206 | 964 |
| 20 | 1652 | 523 |
| 20 | 1708 | 1067 |
| 25 | 1121 | 500 |
| 25 | 652 | 720 |
| 33.3 | 841 | 429 |
| 33.3 | 1141 | 563 |
| 50 | 632 | 315 |
| 50 | 573 | 294 |
| 100 | 304 | 131 |
| 100 | 297 | 244 |

In a further experiment, the effects of the same cholesterol hydroperoxides on the metabolism of acetyl-LDL by mouse peritoneal macrophages was compared. Macrophages were incubated with Compound A (50 μM) or Compound B (25 μM) and $^{125}$I-labelled acetyl-LDL (25 μg in 2 ml) for 6 hr at 37° C. At the end of the incubation, the medium was removed and proteins were precipitated from the medium by addition of trichloroacetic acid. The cells were cooled to 4° C. and treated with buffer containing 10 mM HEPES and heparin to release receptor-bound acetyl-LDL. Finally, the cells were solubilized in 0.1N NaOH and the radioactivities in each fraction were measured. The results are shown in Table 8.

TABLE 8

| | μg Acetyl-LDL/mg protein/6 hr | | |
|---|---|---|---|
| Treatment | heparin-soluble | Intracellular | TCA-soluble |
| Control | 68 = 2 | 583 = 28 | 1899 = 52 |
| Compound A | 125 = 9 | 630 = 34 | 1298 = 91 |
| Compound B | 110 = 25 | 696 = 56 | 1332 = 225 |

Specific activity of $^{125}$I-acetyl LDL, 315 cpm/ng protein.

In still another experiment, inhibition of calmodulin by the same cholesterol hydroperoxides was tested. The calmodulin inhibition was assayed as described by Leung et al. (J. Biol. Chem., 259:2742–2747, 1984). The results are shown in Table 9.

TABLE 9

| Treatment | nmoles phosphate produced | % inhibition |
|---|---|---|
| Compound A. | | |
| 1 μg | 12.1 | 92 |
| 0.1 μg | 16.1 | 68 |
| 0.01 μg | 22.9 | 28 |
| Compound B. | | |
| 1 μg | 13.8 | 81 |
| 0.1 μg | 17.3 | 61 |
| 0.001 μg | 26.9 | 4 |
| No addition | 27.5 | 0 |
| EGTA | 10.7 | 100 |

REFERENCES

Gietzen (1986), in Baker, et al., eds. "Intracellular Calcium Regulation" (Manchester University Press, Manchester, U.K.), pp. 405–423.

Higley et al. (1986), Atherosclerosis, 62: 91–104.

Honda and Komoni (1986), Tetrahedron Lett. 27: 3369–3372.

Leung, et al. (1984), J. Biol. Chem. 259: 2742–2747.

Nes and Varkey (1976), J. Org. Chem., 41: 1652–1653.

Merck Index, The, 9th edition, 1976 (Merck and Co., Inc., Rahway, N.J.), p. 280.

Mather et al. (1985), Biochem. Biophys. Acta, 834: 48.

Mijares, et al. (1967), J. Org. Chem. 32: 810–812.

Peng and Taylor, in Perkins and Visek, eds., "Dietary Fats and Health" (American Oil Chemists Society, Champaign, IL, 1983), pp. 919–933.

Schenck et al. (1958), Leibigs Ann. Chem., 618: 202–211.

Smith (1981), Cholesterol Autoxidation (Plenum Press, New York).

Suckling et al. (1985), J. Lipid Res. 26: 647–741.

Teng et al. (1973), J. Org. Chem., 38: 119–123.

Tipton et al. (1987), Abstract of Paper Presented at the March, 1987, Meeting of American Societies for Experimental Biology; and Tipton et al. (1987), Biochem. and Biophys. Res. Comm., 146: 1166–1172.

van Lier and Rousseau (1976), FEBS Lett. 70: 23–27.

We claim:

1. [A method of suppressing atherogenesis in a human patient, comprising administering to the patient an amount of a cholesterol 20-hydroperoxide selected from the group consisting of 20(R)-hydroperoxy-25-hydroxycholesterol, 20(S)-hydroperoxy-25-hydroxycholesterol and mixtures thereof] *A method of suppressing atherogenesis in a human patient, comprising administering to the patient an amount of a cholesterol hydroperoxide selected from the group consisting of 20-(R)-20,25-dihydroperoxy-3β-hydroxycholest-5-ene, 20-(S)-20,25-dihydroperoxy-3β-hydroxycholest-5-ene and mixtures thereof* effective for reducing aortal deposit of cholesterol, said amount administered being in a dosage range from 0.5 to 25 milligrams of said cholesterol [20-] hydroperoxide per kilogram of body weight per 24 hours.

2. The method of claim 1 in which [the] *said* cholesterol [20-] hydroperoxide is administered orally.

3. A medication for prevention and/or treatment of atherogenesis in human patients, comprising an oral dose form of cholesterol [20-] hydroperoxide[,] *selected from the group consisting of 20-(R)-20,25-dihydroperoxy-3β-hydroxycholest-5-ene, 20-(S)-20,25-dihydroperoxy-3β-hydroxycholest-5-ene and mixtures thereof,* said dose form being selected from tablets and capsules.

4. The medication of claim 3 in which said cholesterol [20-] hydroperoxide is in admixture with a solid carrier.

5. The medication of claim 3 in which said dose form is a tablet, and said cholesterol [20-] hydroperoxide is admixed with a pharmaceutical tabletting composition.

6. The medication of claim 3 in which said dose form is a capsule, and said cholesterol [20-] hydroperoxide is admixed with a pharmaceutical diluent composition.

[7. The medication of claims 3, 4, 5, or 6 in which said cholesterol 20-hydroperoxide is selected from the group consisting of 20(R)-hydroperoxy-25-hydroxycholesterol, 20(S)-hydroperoxy-25-hydroxycholesterol, and mixtures thereof.]

8. [20(R)-hydroperoxy-25-hydroxycholesterol] *20-(R)-20,25-dihydroperoxy-3β-hydroxycholest-5-ene.*

9. [20(S)-hydroperoxy-25-hydroxycholesterol] *20-(S)-20,25-dihydroxyperoxy-3β-hydroxycholest-5-ene.*

* * * * *